United States Patent
Williamson et al.

(10) Patent No.: US 10,426,973 B2
(45) Date of Patent: Oct. 1, 2019

(54) VIVO DRUG DEVELOPMENT AND DELIVERY SYSTEMS AND METHODS

(71) Applicants: Floyd L. Williamson, Athens, AL (US); Zachary J. Shepherd, Baldwinsville, NY (US)

(72) Inventors: Floyd L. Williamson, Athens, AL (US); Zachary J. Shepherd, Baldwinsville, NY (US)

(*) Notice: Subject to any disclaimer, the term of this patent is extended or adjusted under 35 U.S.C. 154(b) by 340 days.

(21) Appl. No.: 15/014,949

(22) Filed: Feb. 3, 2016

(65) Prior Publication Data
US 2016/0151645 A1 Jun. 2, 2016

Related U.S. Application Data

(63) Continuation of application No. 14/139,574, filed on Dec. 23, 2013, now abandoned, which is a
(Continued)

(51) Int. Cl.
*A61N 5/10* (2006.01)
*A61N 5/06* (2006.01)
*A61B 90/00* (2016.01)

(52) U.S. Cl.
CPC .......... *A61N 5/1027* (2013.01); *A61N 5/0601* (2013.01); *A61N 5/062* (2013.01);
(Continued)

(58) Field of Classification Search
CPC ............ A61N 2005/0661; A61N 5/062; A61N 5/1027; A61N 2005/063
See application file for complete search history.

(56) References Cited

U.S. PATENT DOCUMENTS

| 8,834,544 B2 * | 9/2014 | Gerrans | A61K 41/00 607/88 |
| 2003/0229319 A1 * | 12/2003 | Mitchnick | A61L 31/16 604/265 |

(Continued)

OTHER PUBLICATIONS

Williamson vs. Malmay-Bazemore, et al., "Amended Complaint," United States District Court Northern District of Alabama Northeastern Division, Civil Action No. 5:15-cv-01988-HGD, filed on Mar. 18, 2016.

(Continued)

*Primary Examiner* — Deanna K Hall
(74) *Attorney, Agent, or Firm* — Patent Grove LLC; Tomas Friend

(57) ABSTRACT

The present disclosure generally pertains to in vivo drug development and delivery systems and methods. The systems include a hollow tubular assembly with a chamber for receiving and transmitting an ionizing substrate solution, and a structure to transmit non-radioactive ionizing radiation to the ionizing substrate solution. The resulting free radical drug is transferred directly into a patient treatment site through an applicator. The systems and methods described herein provide simple, inexpensive techniques for in vivo production of an optimal chemotherapeutic drug without the use of radioactive radiation and directly injecting the drug into the patient's tissue with very minimal systemic side-effects.

10 Claims, 8 Drawing Sheets

Related U.S. Application Data continuation-in-part of application No. 13/917,522, filed on Jun. 13, 2013, now abandoned.

(60) Provisional application No. 61/659,077, filed on Jun. 13, 2012.

(52) U.S. Cl.
CPC . *A61B 2090/378* (2016.02); *A61N 2005/0612* (2013.01); *A61N 2005/0661* (2013.01); *A61N 2005/1021* (2013.01)

(56) References Cited

U.S. PATENT DOCUMENTS

| | | |
|---|---|---|
| 2009/0169591 A1 | 7/2009 | Kaul et al. |
| 2012/0259152 A1 | 10/2012 | Gerrans et al. |
| 2012/0282185 A1 | 11/2012 | Dobson et al. |
| 2013/0017266 A1 | 1/2013 | Ogino et al. |
| 2014/0371710 A1 | 12/2014 | Williamson et al. |

OTHER PUBLICATIONS

Kito, et al., "Hydrogen Peroxide & UV Treatment," California Polytechnic State University, pp. 1-6.
Munter, "Advanced Oxidation Processes—Current Status and Prospects," Proc. Estonian Acad. Sci. Chem., 2001, 50, 2, 59-80.
Dewaele, et al., "ROS-Mediated Mechanisms of Autophagy Stimulation and their Relevance in Cancer Therapy 6:7," pp. 838-854, Oct. 1, 2010.

\* cited by examiner

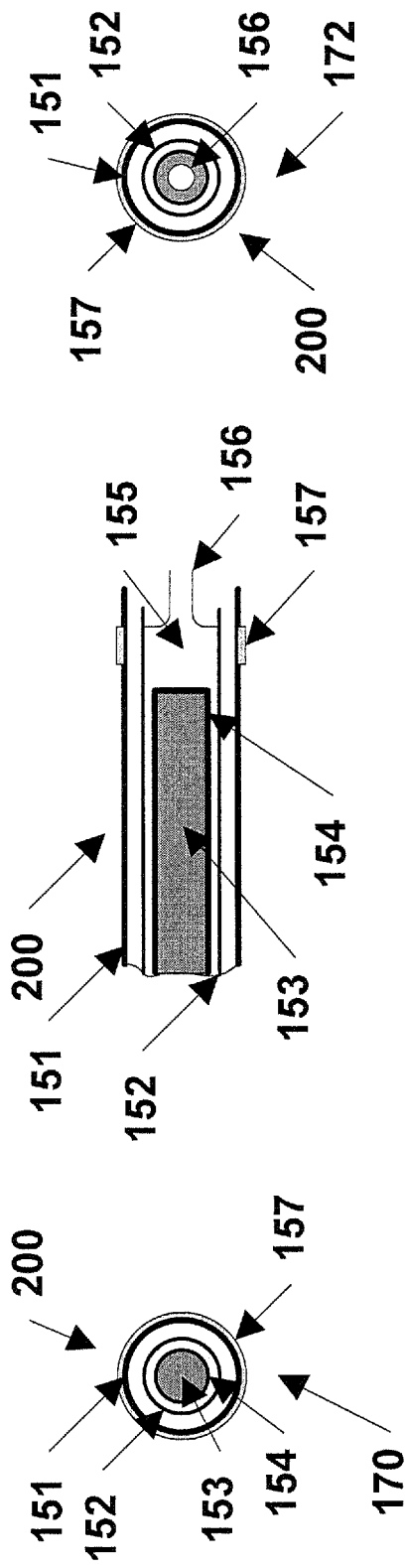

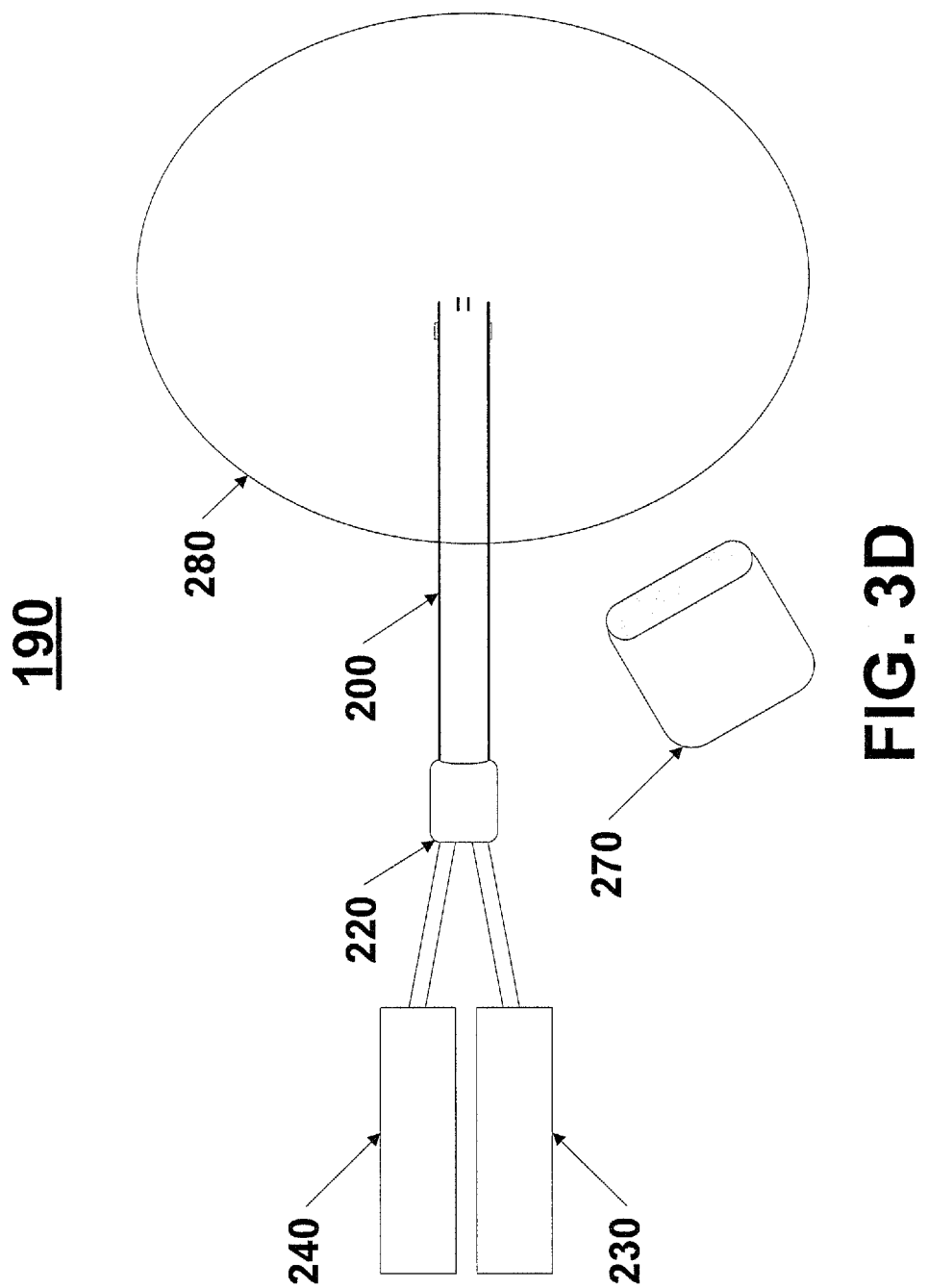

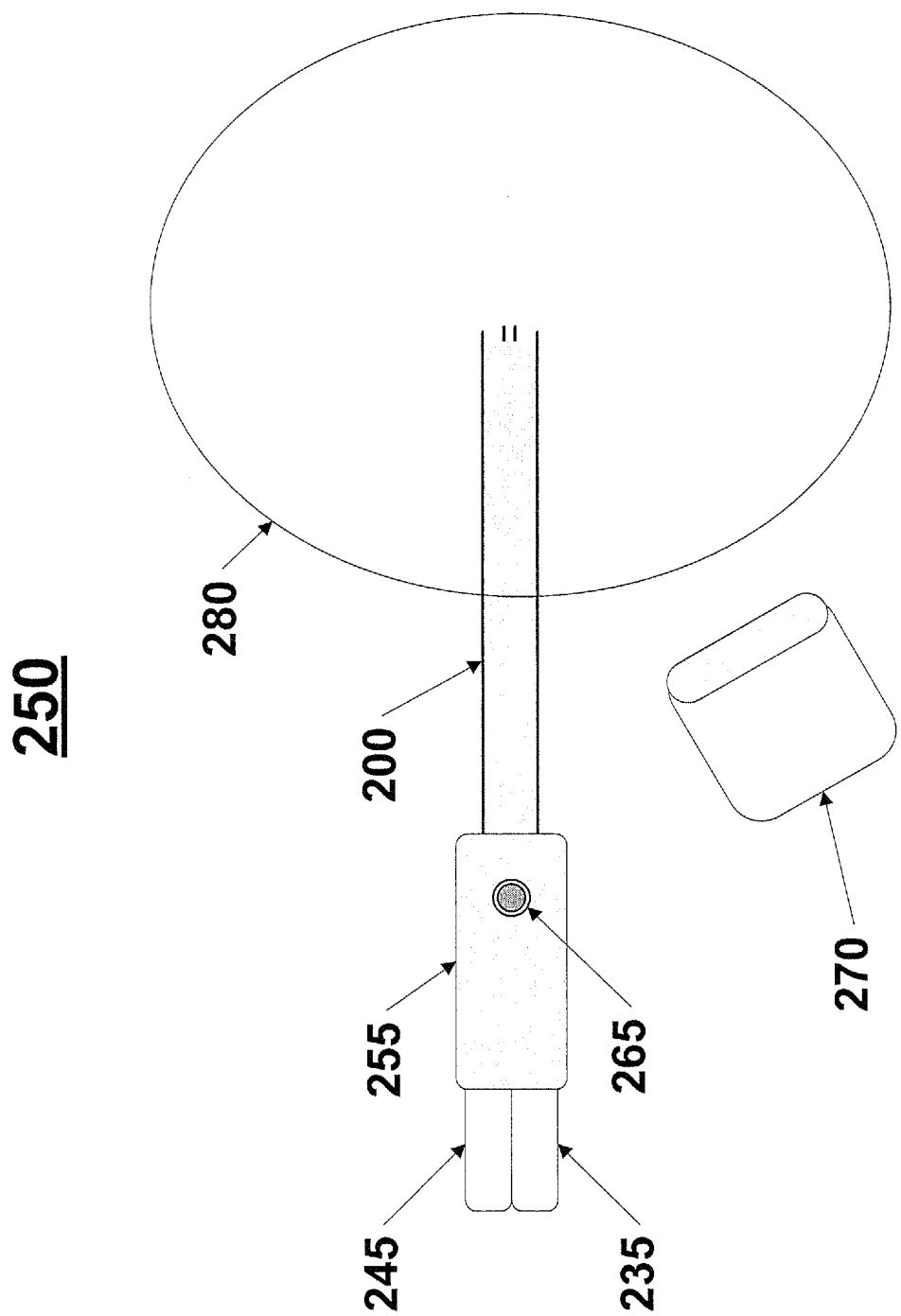

VIVO DRUG DEVELOPMENT AND DELIVERY SYSTEMS AND METHODS

CROSS REFERENCE TO RELATED APPLICATION

This application is a continuation of and claims priority to U.S. patent application Ser. No. 14/139,574, entitled, "In Vivo Druq Development and Delivery Systems and Methods," and filed on Dec. 23, 2013, which is incorporated herein by reference. U.S. patent application Ser. No. 14/139,574 is a continuation-in-part of and claims priority to U.S. patent application Ser. No. 13/917,522, entitled, "Drug Delivery and Treatment Systems and Methods" and filed on Jun. 13, 2013, which is incorporated herein by reference. U.S. patent application Ser. No. 14/139,574 also claims priority to U.S. Provisional Patent Application No. 61/912,110, entitled "In Vivo Drug Development and Treatment Systems and Methods," and filed on Dec. 5, 2013, which is incorporated herein by reference, and U.S. Provisional Patent Application No. 61/918,515, entitled "In Vivo Drug Development and Treatment Systems and Methods," and filed on Dec. 19, 2013, which is incorporated herein by reference. U.S. patent application Ser. No. 13/917,522 claims priority to U.S. Patent Provisional Application 61/659,077, entitled "Drug Delivery and Treatment Systems and Methods," and filed on Jun. 13, 2012, which is incorporated herein by reference.

RELATED ART

Cancer is an insidious and complex disease requiring multiple modality options. The three prevailing treatment options include surgery, chemotherapy, and nuclear or radioactive radiation. Surgical procedures, such as debulking, remove a portion of a malignant tumor, but it is often difficult to eliminate all of the diseased tissue such that the tumor returns. Radiotherapy includes irradiation, radiation therapy, or radiation oncology and is defined as the use of ionizing radioactive radiation to treat disease, kill cancer cells, or shrink tumors. Chemotherapy is the use of chemicals to treat disease, which is not limited to cancer. All three procedures have advantages as well as serious systemic consequences. There are many different types of cancers, as well as other diseases, each requiring individual treatment options utilizing a combination of the above-described therapies.

Many cancer patients receive at least one form of radiotherapy during their treatment cycle. Traditionally, radiotherapy is conducted in specialized facilities at a significant cost, sometimes on the order of hundreds of thousands of dollars per patient. Ionizing radiation is produced when a particle, such as a photon, acquires enough energy to remove an electron from an atom or molecule. Ionizing radiation is a biological and environmental hazard. Direct ionizing radiation describes charged particles (electrons, protons, and alpha particles) with sufficient energy to produce ionization by collision. Indirect ionizing radiation generally refers to the use of uncharged particles (neutrons and photons) to liberate particles by direct ionization. Radiotherapy generally involves the use of indirect radiation for the generation of free radicals, such as hydroxyl radicals, which then damage cancerous or diseased cells.

The energy level of an electromagnetic particle is indirectly proportional to its wavelength. For example, gamma rays with wavelengths of 50 fm have an energy level of about 25 MeV; x-rays with 50 pm wavelength yield about 25 keV; ultraviolet light with a wavelength of 100 nm yields about 12 eV; visible light with a wavelength of 550 nm yields about 2 eV; and microwaves with 1 cm wavelength exhibit roughly 120 $\mu$eV.

One major obstacle in the treatment of aggressive cancers is the fact that these cancers require chemotherapeutic or radiotherapeutic doses that are harmful or fatal to the patient. Treatment of cancer is systemic, where the cytotoxic drugs or radiation attack both malignant cells and healthy tissues. Selectively targeting the diseased cells is very difficult. In addition, radiation or chemotherapy treatment suppresses the immune system and therefore makes the patient susceptible to a host of other diseases. An additional complication is the fact that the patient's body adapts to the treatment and becomes resistant to further therapy.

Glioblastoma multiforme (GBM) tumors are the most common and aggressive malignant brain tumors in humans and are classified by the World Health Organization (WHO) as Grade IV tumors. Most GBM tumors originate in the deep white matter of the brain and quickly infiltrate other areas of the brain and the body. GBM tumors may grow very large before symptoms become apparent. GBM tumors are one of the most aggressive, resulting in a typical survival rate of less than a year after diagnosis. Treatment of these types of tumors is generally palliative, i.e., focusing on relieving and preventing the suffering of the patient, as there is no cure currently available. Recurrent tumors usually occur within 2 cm of the original tumor post treatment, which generally involves surgery followed by radiation and chemotherapy. GBM tumors are very resistant to chemotherapy. Aggressive radiation or chemotherapy treatment of recurrent tumors is difficult because the health of the patient is compromised and further procedures will shorten survival time. Patients suffering from GBM tumors and other cancers, such as pancreatic cancer, typically have poor prognosis as the available treatment options become too toxic and ineffective for continued treatment.

What is needed in the art, therefore, is a targeted, localized, minimally invasive cancer treatment which is readily available, causes fewer side effects for the patient and can be periodically repeated as needed to prevent the reoccurrence of the cancer.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 3A is an anterior cross sectional view of one embodiment of the system of the present disclosure.

FIG. 3B is a cross sectional view of one embodiment of the system of the present disclosure.

FIG. 3C is a posterior cross sectional view of one embodiment of the system of the present disclosure.

FIG. 3D is a perspective view of one embodiment of the system of the present disclosure.

FIG. 5B is a perspective view of one embodiment of the system of the present disclosure.

DETAILED DESCRIPTION

The present disclosure generally pertains to systems and methods for in vivo production of free radicals from a solution for the treatment of certain medical conditions. In one embodiment, hydroxyl radicals are produced from inexpensive medical grade hydrogen peroxide. The systems and methods allow for the targeted, localized, minimally invasive treatment of a variety of medical ailments. In addition, the described methods utilize an inexpensive process which can significantly affect the survival rates and survival times for those who suffer from a variety of diseases where conventional treatments are ineffective.

Unstable particles, such as gamma or x-rays, are classified as radioactive because they exhibit excess energy, mass, or both. To reach stability they must give off or emit the excess energy or mass. One embodiment of the present disclosure utilizes non-radioactive ultraviolet electromagnetic radiation (photons).

Figure 1:
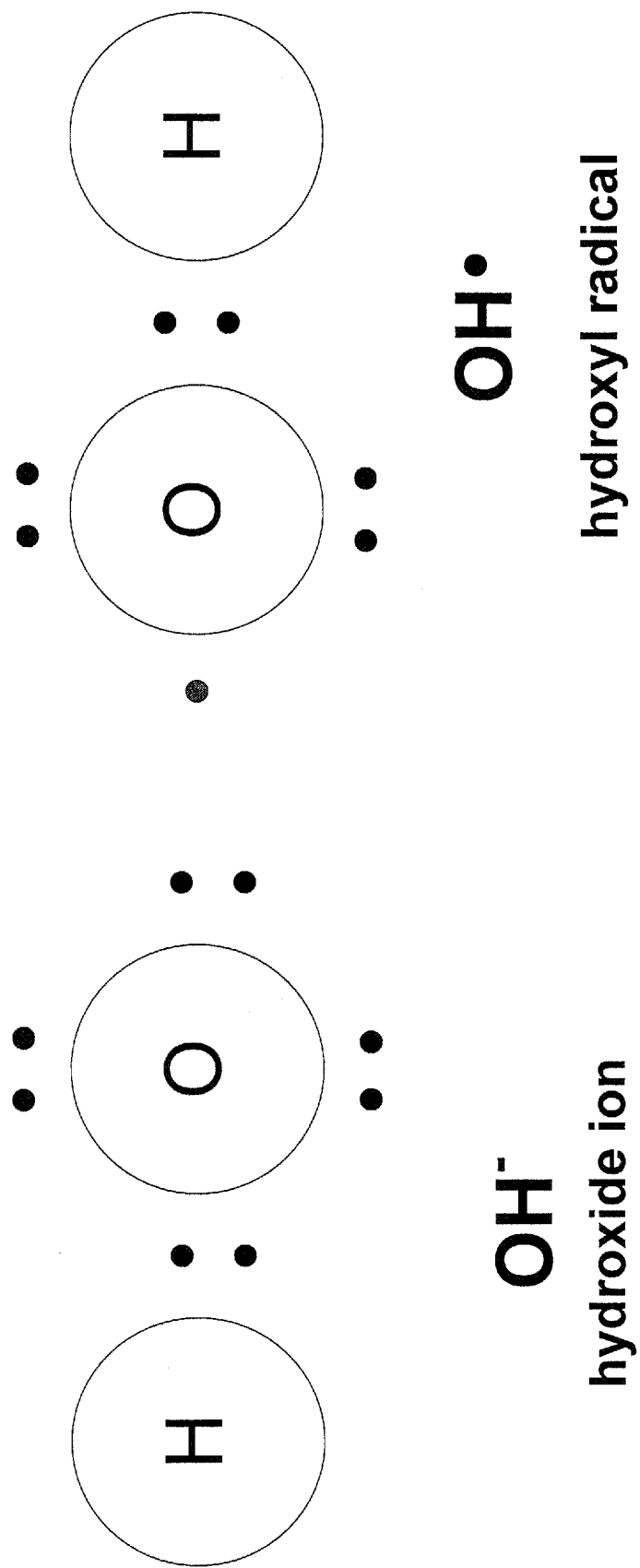
FIG. 1 illustrates the two forms of the hydroxyl molecule.

One embodiment of the present disclosure utilizes free radicals which are unstable atoms, ions, or molecules containing unpaired electrons. Biological systems produce radicals, which are used to kill invading pathogens and mutant cells. This action is defined as the reactive oxygen species (ROS). Antioxidants, such as vitamin C and vitamin E, act to counteract free radical damage in the body. ROS also form as a by-product of metabolism. Free radicals include atoms, molecules, or ions with unpaired valence electrons or open electron shells. One embodiment of the present disclosure utilizes the radical form of the hydroxyl molecule. The hydroxyl molecule exists in two forms: the hydroxide ion ($OH^-$) and hydroxyl radical (OH.). FIG. 1 illustrates the two forms of the hydroxyl molecule. While hydroxide is an ion with a negative charge (anion), the hydroxyl radical is charge neutral. Hydroxyl radicals exhibit extremely fast reaction rates and kinetics. The in vivo half-life is roughly one billionth of a second.

Figure 2:
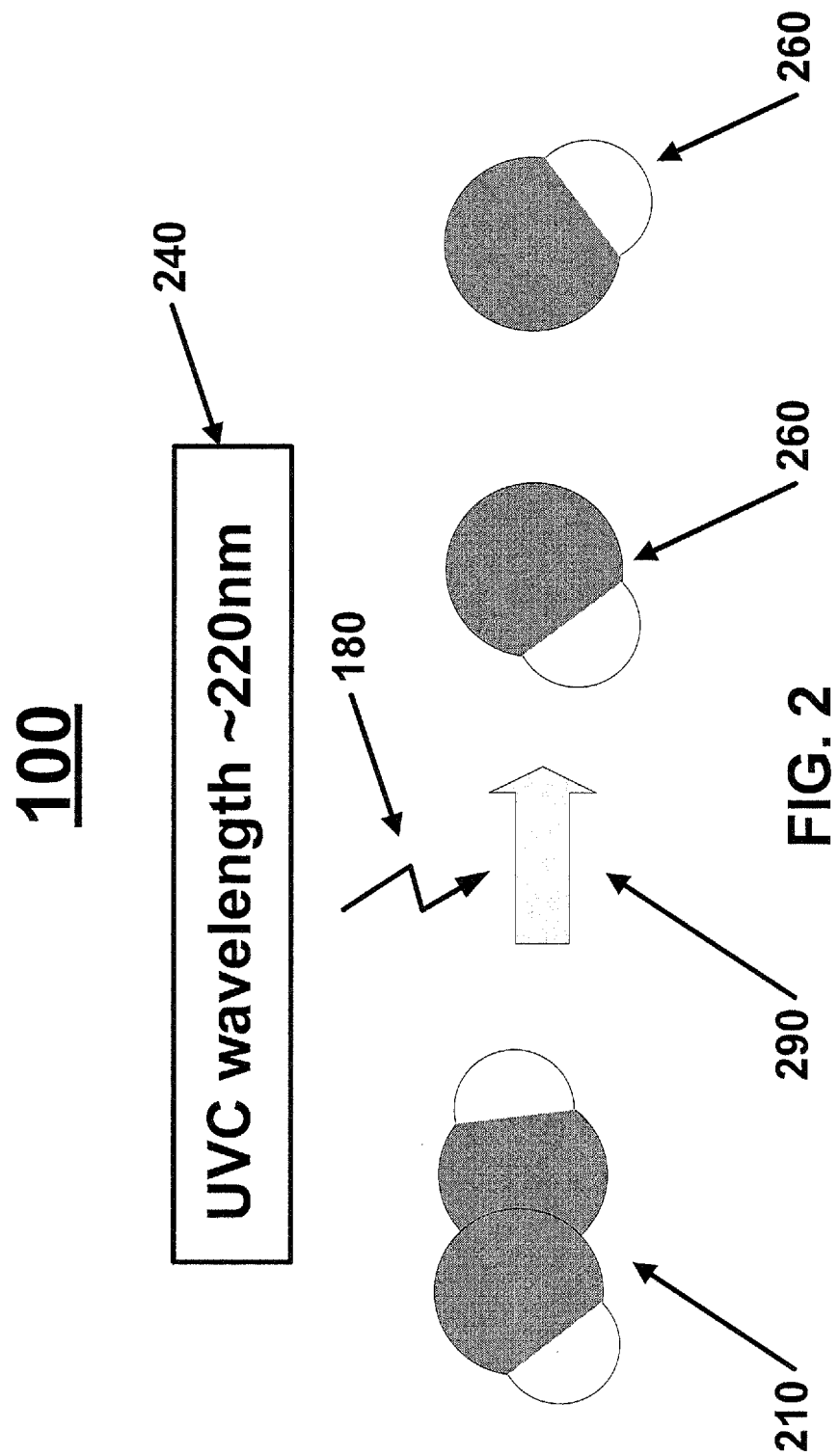
FIG. 2 illustrates a process of generating two hydroxyl radicals (OH.) from a single $H_2O_2$ molecule through the use of non-radioactive ionizing radiation.

In one embodiment, the present systems and methods utilize the production of hydroxyl radicals (OH.) generated from hydrogen peroxide ($H_2O_2$) via exposure to subtype C ultraviolet light. Generation of the radicals may be accomplished through the use ultraviolet electromagnetic radiation subtype C (UVC) with a wavelength of approximately 220 nanometers (nm). This process is similar to one technique used in Advanced Oxidation Process (AOP), a chemical treatment process designed to kill or destroy organic materials in water and waste water by oxidation through reactions with hydroxyl radicals. UVC is a non-radioactive type of ionizing radiation. FIG. 2 illustrates process 100 generating two hydroxyl radicals 260 (OH.) from a single molecule of an ionizable substrate solution 210 ($H_2O_2$ molecule) in chemical reaction 290 after exposure to UVC ionizing radiation 180. UVC radiation source 240 generates the predetermined UVC ionizing radiation 180 with a wavelength of roughly 220 nm. Note that substances other than hydrogen peroxide may be used to produce hydroxyl radicals. As an example, hydroxyl radicals may be developed by irradiating water. However, high energy radiation is required to develop hydroxyl radicals from water.

FIGS. 3A-3D illustrate an embodiment of in vivo drug development and delivery systems 150 and 190 of the present disclosure. System 150 includes a drug delivery device 200 with an outer cannula 151 surrounding an inner cannula 152. As used herein, a cannula is a tube that can be inserted into the patient's body for the delivery or removal of fluids. The system 190 includes a cable-hose assembly 220 extending from the posterior end 170 of device 200 (FIG. 3D). In this embodiment, a fluid is pumped through cable-hose assembly 220 by the application of pressure, where it then travels into device 200 and is deposited in preparation chamber 155 for exposure to ionizing radiation 180. The fluid is then deposited into treatment area 280. Optionally, cable-hose assembly 220 could include an external vacuum or suction function for removal of fluids and materials (vacuum equipment not shown). Referring again to FIGS. 3A-3D, the posterior end 170 of device 200 includes ports for electrical connections and other devices (not shown) or connection areas for attachment to hoses (FIG. 3D). Anterior end 172 of device 200 makes contact with and enters the patient treatment area 280 for the production and application of the generated hydroxyl radicals, which chemically react (oxidization process) with the living tissue in treatment area 280.

Outer cannula 151, inner cannula 152, radiation cable 153, and applicator 156 define an inner chamber 155 within device 200. Inner chamber 155 receives precise, metered doses of the solution containing an ionizable substrate. As used herein, an ionizable substrate solution is a fluid that contains molecules which are converted to a free radical upon exposure to ionizing radiation. In one embodiment, the solution containing an ionizable substrate is a hydrogen peroxide solution. The substrate solution in chamber 155 is exposed to ionizing radiation via radiation cable 153, as will be described in greater detail below. In one embodiment, the transmitted ionizing radiation 180 is UVC radiation. Chamber 155 is positioned at the anterior end 172 of device 200 and acts as an ionizing radiation preparation chamber 155 for irradiation of precise, metered doses of ionizable substrate solution 210. In the example illustrated in FIGS. 3A-3D, the radiation cable 153 for transmitting externally generated ionizing radiation 180 is an optical fiber. The radiation cable 153 transmits externally generated ionizing radiation 180 to inner chamber 155. The radiation cable 153 extends from the posterior end 170 of device 200 and terminates at the ionizing radiation preparation chamber 155. In this embodiment, a cable sheath 154 envelops radiation cable 153 to secure and protect the conductors. The radiation cable 153 directs the ionizable radiation 180 to the ionizing substrate solution 210 residing in chamber 155.

Outer cannula 151 serves as a main structural element of device 200 and, in conjunction with the outer surface of inner cannula 152, forms an optional vacuum-assisted suction cannula for extraction of materials or application of other solutions, as directed by a physician, at the patient treatment area 280. In one embodiment, the size of outer cannula 151 is that of a #16 gauge needle and inner cannula 152 is typically the size of a #32 gauge needle, although other sizes are possible in other embodiments. Device 200 may be supplied in different lengths, typically ranging from about 6 to about 300 mm although any practical length may be fabricated to accommodate access to different areas of the patient's body.

Applicator 156 is positioned at the anterior end 172 of the device 200 (FIG. 3C). In one embodiment, applicator 156 is constructed from a rigid or semi-rigid material which will not react with the free radical solution. In one embodiment, applicator 156 is constructed from glass or ceramic, although other materials are possible. The material utilized to fabricate cannula 151 should exhibit sufficient strength and rigidity to allow device 200 to pierce the skin and tissue of the patient. In one embodiment, applicator 156 is constructed as a hollow tubular structure through which the produced free radical drug may travel.

Referring to FIGS. 3A-3D, the pressure control element 230 pumps a predetermined, precise, metered dose of ionizable substrate solution 210 into preparation chamber 155. The radiation source 240 generates a predetermined wavelength of ionizing radiation (illustrated in FIG. 2). Radiation cable 153 (e.g., optical fiber) is positioned to transmit the ionization radiation to preparation chamber 155 where irradiation of the ionizable substrate solution 210 occurs. Irradiation of the ionizable substrate solution 210 in chamber 155 will produce a precise, metered dose of free radical drug 260. Activation of the pump control element 230 will advance another precise, metered dose of ionizable substrate solution 210 into chamber 155, thereby expelling the previously produced free radical drug 260 from chamber 155 via applicator 156. As an example, the predetermined metered doses of solution 210 will be in the range of microliters (µl), thus the predetermined metered doses of drug 260 will also be in microliters. Individual doses of drug 260, in the range of microliters will effectively treat an area in the range of tens to hundreds of $mm^3$. This process will be repeated as necessary to achieve the desired treatment plan.

To ensure the effective localization of the treatment of diseased tissue and minimize damage to healthy tissue, external imaging apparatus 270 (FIG. 3D) may be used to guide the accurate placement of device 200. In many cases, treatment area 280 will be larger than the area suitable for a metered dose of drug 260. As a result, device 200 will be repositioned within the patient and additional amounts of drug 260 will be produced and applied repeatedly as needed to ensure accurate treatment of the designated treatment area 280. In one embodiment, imaging apparatus 270 may be as simple as a portable ultrasonic imaging device. In an additional embodiment, outer cannula 151 incorporates an optional embedded marker 157 that allows use of complex external imaging apparatus 270 to ensure precision three dimensional placement of device 200 within treatment area 280.

In one embodiment, applicator 156, inner cannula 152 and optional cable sheath 154 are fabricated from a chemically-resistant material, for example glass. All components that contact the patient will be constructed from biologically compatible materials which will not cause adverse reactions inside the body. Device 200 may be discarded after use.

Figure 4:
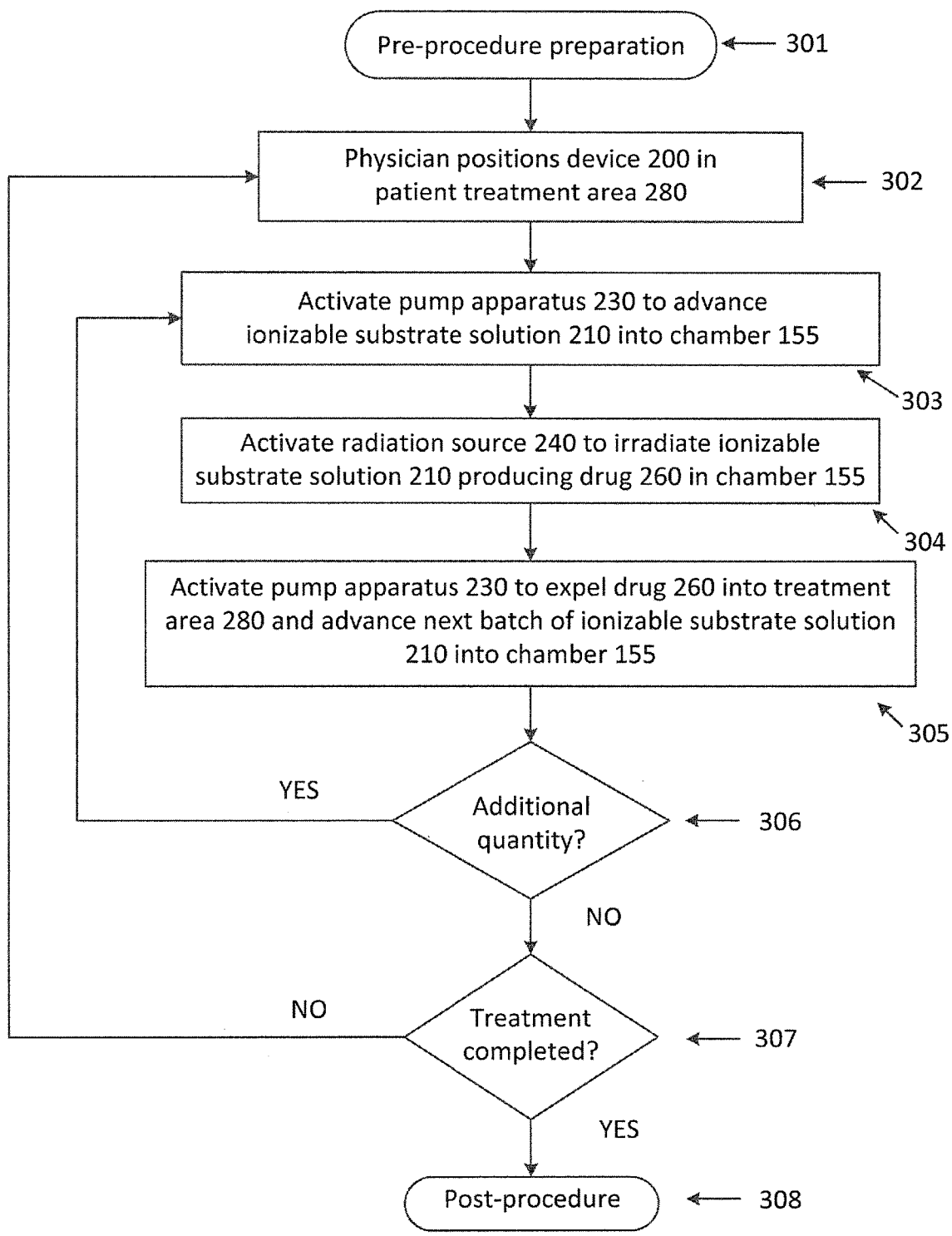
FIG. 4 is a flow chart illustrating a method for in vivo production and administration of free radicals.

FIG. 4 is a simplified flow diagram describing a method of one embodiment illustrated in FIGS. 3A-3D of the present disclosure. The pre-procedure preparation process begins at step 301. This procedure is similar in complexity to a needle biopsy so the treatment pre-procedure preparation with be similar to the equivalent needle biopsy preparation. As an example, a needle biopsy of the brain is more complex than a liver needle biopsy so treatment of a brain tumor will logically be more complicated than treating a liver tumor. This method can be used to treat any localized treatment area of the body where targeted tissue can be identified with external imaging technology or other technique. This procedure is not suitable for any area of the body where a needle biopsy is contraindicated such as the brain stem. The complexity of the treatment procedure will dictate the pre-procedure preparation. The size and location of the treatment area(s) will also determine the complexity of the procedure and degree of care needed to keep the patient comfortable. Similarly, the physician may administer antibiotics or other drugs to prevent medical complications as is standard operating practice during many needle biopsies. This method may be performed in standard out-patient surgical facilities and in some cases a physician's office or mobile care facility.

Referring again to FIG. 4, the physician guides the placement of device 200 (FIG. 3D) into the patient treatment area 280 at step 302. Placement of device 200 may include the use of an external imaging apparatus 270 (FIG. 3D). The external imaging apparatus may be guided by the use optional embedded marker 157 for precise placement of device 200. Device 200 is inserted into the patient's body to access treatment area 280. The diameter of device 200 is on the order of a #16 gauge needle although other diameters are possible. A small diameter for device 200 is desirable to help ensure a minimally invasive procedure. In step 303, pump apparatus 230 is activated to advance a precise, metered dose of ionizable substrate solution 210 from pump apparatus 230 to cable-hose assembly 220 for transfer to device 200. A precise, metered dose of ionizable substrate solution 210 then advances to preparation chamber 155. In this embodiment, the ionizable substrate solution 210 is a hydrogen peroxide solution ($H_2O_2$). In step 304, radiation source 240 is activated and the ionizing radiation 180 travels through the cable-hose assembly 220 and radiation cable 153 to irradiate the ionizable substrate solution 210 in preparation chamber 155. In this embodiment, the ionizing radiation is subtype C ultraviolet electromagnetic radiation (UVC) with a wavelength of roughly 220 nm. Radiation source 240 is a generator (e.g., lamp) capable of generating UVC electromagnetic radiation with wavelength of roughly 220 nm. In one embodiment, radiation cable 153 is an optical fiber capable of transmitting UVC radiation with a wavelength of roughly 220 nm. As illustrated in FIG. 2, exposing the ionizable substrate solution 210 to ionizing radiation 180 will cause a chemical reaction 290 that will produce two free radical drugs 260 from each molecule of ionizable substrate solution 210. In this embodiment, two hydroxyl radicals (free radical drug 260) are produced in chamber 155 from each molecule of hydrogen peroxide. In step 305, the pump apparatus 230 is activated, expelling the free radical drug 260 into the treatment area 280 via applicator 156. The volume of the dispensed free radical drug 260 is generally in the range of microliters, although any practical quantity may be produced. At the same time, activation of the pump apparatus 230, in step, 305 also advances the next precise, metered dose of ionizable substrate solution 210 into chamber 155. In step 306, the physician determines if additional volumes of the free radical drug 260 are desired. If more free radical drug is desired, steps 303 through 305 may be repeated to generate additional doses to be dispensed into the patient treatment area 280. The procedure advances to step 307 if the physician determines that an adequate amount of free radical drug 260 has been deposited into treatment area 280. In step 307, the physician can decide to repeat steps 302-306 as needed to achieve the overall treatment plan. Steps 303 to 305 typically treat an area in the range of tens to hundreds of cubic millimeters ($mm^3$) based on doses in the range of microliters. Steps 302-307 allow the treatment of any practical-size treatment area 280. The procedure terminates at step 308 and the post-procedure and post-care of the patient begins.

Figure 5A:
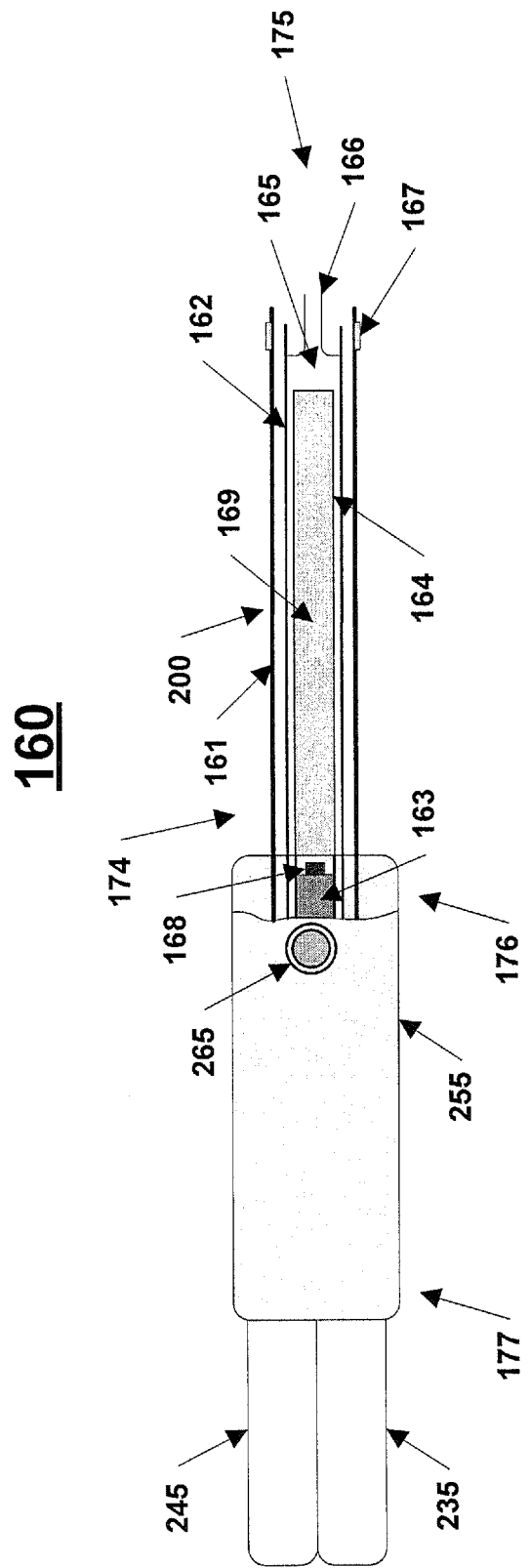
FIG. 5A is a cross sectional view of an additional embodiment of the system of the present disclosure.

FIGS. 5A-5B illustrate an embodiment of a portable in vivo drug development and delivery systems 160 and 250 of the present disclosure. System 160 includes a drug development and delivery device 200 with an outer cannula 161 surrounding an inner cannula 162. Device 200 functions exactly as described with reference to systems 150 and 190.

Systems 160 and 250 include a portable control device 255 connected to the posterior end 174 of device 200 (FIG. 5A). Pump control cartridge 235 and power pack 245 are replaceable cartridges connected to portable control device 255. Pump control pack 235 contains sufficient quantities of ionizable substrate solution 210 to develop many doses of free radical drug 260. Power pack 245 supplies sufficient power for extended operation of systems 160 and 250. In this embodiment, a fluid is pumped from pump control pack 235 through portable control device 255 by the application of vacuum or pressure. The fluid then travels into device 200 and is deposited in preparation chamber 165 for exposure to ionizing radiation 180. The fluid is then pumped into treatment area 280. Optionally, systems 160 and 190 may include external vacuum or suction functions for removal of fluids and materials (vacuum equipment not shown). Anterior end 175 of device 200 makes contact with and enters the patient treatment area 280 for application of the generated hydroxyl radicals which chemically react (in an oxidization process) with the living tissue in treatment area 280.

Referring to FIG. 5A, outer cannula 161, inner cannula 162, radiation cable 169 and applicator 166 define an inner chamber 165 in device 200. Inner chamber 165 receives precise, metered doses of the ionizable substrate solution 210. As used herein, an ionizable substrate solution 210 is a fluid that contains molecules which are converted to a free radical upon exposure to ionizing radiation. In one embodiment, the solution containing an ionizable substrate is a hydrogen peroxide solution.

The substrate solution in chamber 165 is exposed to ionizing radiation 180 via radiation cable 169. In one embodiment, the transmitted ionizing radiation 180 is UVC radiation with wavelength of roughly 220 nm, although other wavelengths are possible in other embodiments. Chamber 165 is positioned at the anterior end 175 of device 200 and acts as an ionizing radiation preparation chamber 165 for irradiation of precise, metered doses of ionizable substrate solution 210. In the example illustrated in FIGS. 5A-5B, the radiation cable 169 used to transmit the generated ionizing radiation 180 is an optical fiber. Radiation cable 169 transmits the generated ionizing radiation 180 to chamber 165 and extends from the posterior end 174 of device 200 terminating at the ionizing radiation preparation chamber 165. In this embodiment, a cable sheath 164 envelops the radiation cable 169 to secure and protect the conductors. The optical fiber 169 directs the ionizable radiation 180 to the ionizing substrate solution 210 residing in chamber 165.

Outer cannula 161 serves as a main structural element of device 200 and, in conjunction with the outer surface of inner cannula 162, forms an optional vacuum-assisted suction cannula for extraction of materials or application of other solutions, as directed by a physician, at the patient treatment area 280. In one embodiment, the size of outer cannula 161 is that of a #16 gauge needle and inner cannula 162 is typically the size of a #32 gauge needle, although other sizes are possible in other embodiments. Device 200 may be constructed in different lengths, typically ranging from about 6 to about 300 mm, although any practical length may be fabricated to accommodate access to different areas of the patient's body.

Applicator 166 is positioned at the anterior end 175 of device 200 (FIG. 5A). In one embodiment, applicator 166 is constructed from a rigid or semi-rigid material which will not react with the free radical solution. In one embodiment, applicator 166 is constructed from glass or ceramic, although other materials are possible. The material utilized to fabricate cannula 161 should exhibit sufficient strength and rigidity to allow device 200 to pierce the skin and tissue of the patient.

Referring to FIG. 5A, portable control device 255 includes electronic subassembly 163, UVC LED 168, and switch 265 (as well as ports for connection to device 200), pump control apparatus 235, and power pack 245. Additionally, portable control device 255 may also include ports for connection to delivery device 200. Device 200 is connected to the anterior end 176 of portable control device 255, and pump control apparatus 235 and power pack 245 are connected to anterior end 177 of portable control device 255. UVC LED 168 is mounted on electronic subassembly 163. In this embodiment, UVC LED 168 is an LED capable of radiating UVC radiation at a wavelength of roughly 220 nm. Electronic subassembly 163 controls the operation of UVC LED 168, switch 265, and pump control apparatus 235. Activation of switch 265 causes electronic subassembly 163 to advance a precise, metered dose of ionizable substrate solution 210 from pump control apparatus 235 through device 200 into preparation chamber 165, while concurrently expelling the previously produced radical drug 260 in chamber 165 via applicator 166. At the same time, electronic subassembly 163 powers LED 168 generating ionizing radiation 180 that travels via radiation cable 169 to irradiate the ionizable substrate solution 210 in chamber 165, producing two molecules of radical drug 260 from each molecule of substrate solution. As an example, the predetermined metered doses of solution 210 will be in the range of microliters (μl), and therefore the predetermined metered doses of drug 260 will also be in the range of microliters. Individual doses of drug 260, in the range of microliters, will effectively treat an area in the range of tens to hundreds of $mm^3$. This process will be repeated as necessary to achieve the desired treatment plan.

To ensure the effective localization of the treatment in treatment area 280 and reduce damage to healthy tissue, external imaging apparatus 270 (FIG. 5B) may be used to guide the accurate placement of device 200. In many cases, treatment area 280 will be larger than suitable for a metered dose of drug 260 so that device 200 will be repositioned and drug 260 will be produced and applied repeatedly as needed to ensure accurate treatment of the designated treatment area 280. In one embodiment, imaging apparatus 270 may be as simple as a portable ultrasonic imaging device. In an additional embodiment, outer cannula 161 incorporates an optional embedded marker 167 that allows use of complex external imaging apparatus 270 to ensure precision three dimensional placement of device 200 within treatment area 280. In one embodiment, applicator 166, inner cannula 162, and optional cable sheath 164 are fabricated from a chemically-resistant material, for example glass. Preferably, all components that may contact the patient will be constructed from biologically compatible materials which will not cause adverse reactions inside the body of the patient. Device 200 is normally discarded after use.

Figure 6:
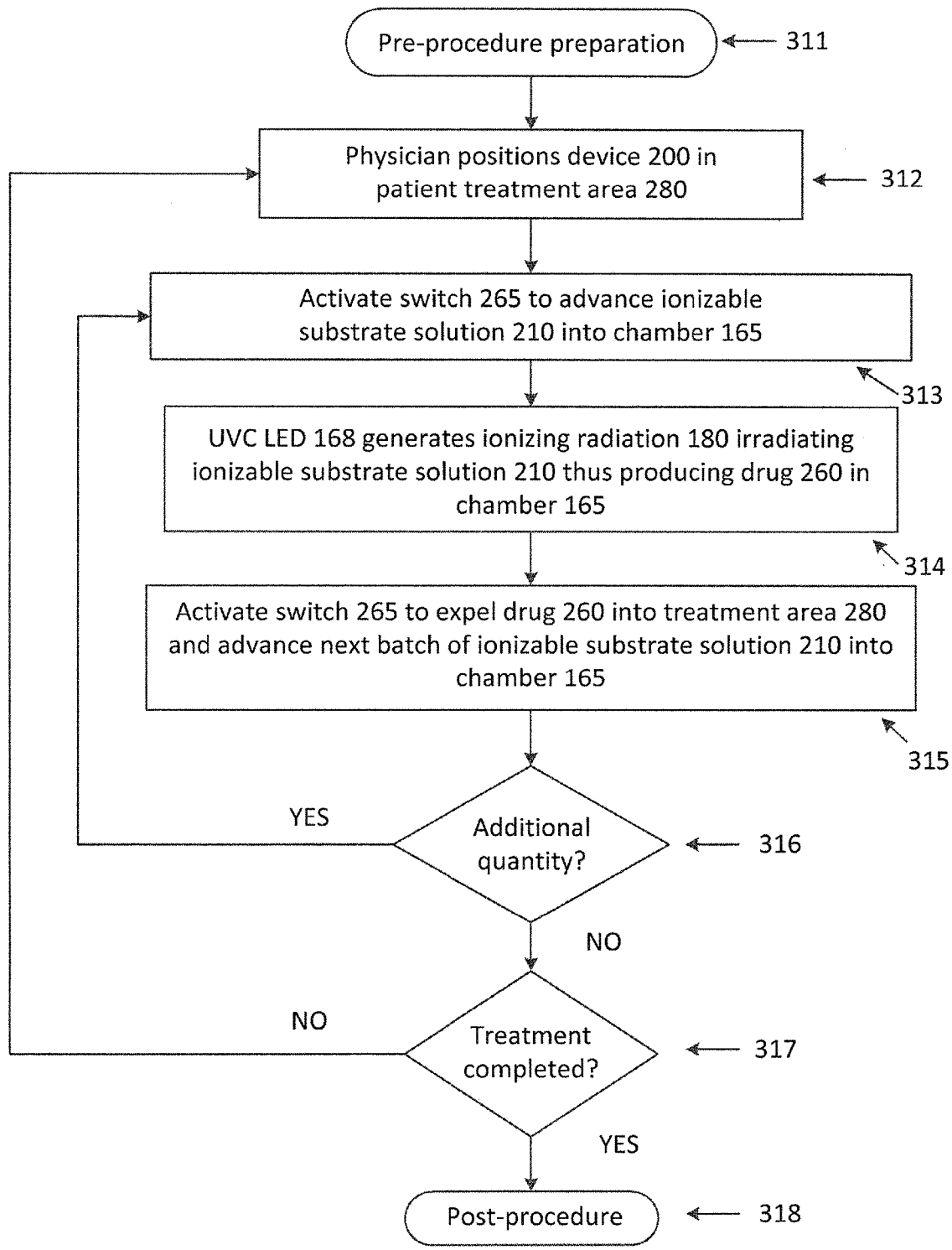
FIG. 6 is a flow chart illustrating a method for in vivo production and administration of free radicals.

FIG. 6 is a flow diagram describing the method of one embodiment illustrated in FIGS. 5A-5B of the present disclosure. The pre-preparation process begins at step 311. This method is similar in complexity to a needle biopsy so the pre-procedure preparation with be similar to the equivalent needle biopsy preparation. As an example, a needle biopsy of the brain is more complex than a liver needle biopsy so treatment of a brain tumor will logically be more complicated than treating a liver tumor. This method can be used to treat any localized treatment area of the body where targeted tissue can be identified with external imaging technology or other technique. This procedure is not suitable for any area of the body where a needle biopsy is contraindicated such as the brain stem. The complexity of the treatment procedure will dictate the pre-procedure preparation. The size and location of the treatment area(s) will also determine the complexity of the procedure and degree of care needed to keep the patient comfortable. Similarly, the physician may administer antibiotics or other drugs to prevent medical complications as is standard practice during a needle biopsy. This treatment method may be performed in standard out-patient surgical facilities or in some cases a physician's office or mobile care facility.

As outlined in step 302, the physician guides the placement of device 200 (FIG. 5B) into the patient treatment area 280. Placement of device 200 may include the use of an external imaging apparatus 270 (FIG. 5B), and as desired the external imaging apparatus may be guided by the use of optional embedded marker 167 for precise placement of device 200. Device 200 is inserted into the patient's body to access treatment area 280. The diameter of device 200 is on the order of a #16 gauge needle although other diameters are possible. A small diameter for device 200 is desired to help ensure that the procedure remains minimally invasive. In step 313, pump apparatus 235 is activated by switch 265 to advance a precise, metered dose of ionizable substrate solution 210 from pump control apparatus 235 to portable control device 255. The solution 210 is then transferred to device 200. A precise, metered dose of ionizable solution 210 advances to preparation chamber 165. In this embodiment, the ionizable substrate solution 210 is a hydrogen peroxide solution ($H_2O_2$). In step 314, radiation source 240 (UVC LED 168) is activated by switch 265 and the ionizing radiation 180 travels through the radiation cable 169 to irradiate the ionizable substrate solution 210 in preparation chamber 165. In this embodiment, radiation source 240 is a UVC LED 168 capable of generating ionizing radiation 180 with a wavelength of roughly 220 nm, thus producing ionizing radiation 180 as subtype C ultraviolet electromagnetic radiation (UVC) with a wavelength of roughly 220 nm. In one embodiment, radiation cable 169 is an optical fiber capable of transmitting UVC radiation with a wavelength of roughly 220 nm. As illustrated in FIG. 2, exposing the ionizable substrate solution 210 to ionizing radiation 180 will cause a chemical reaction 290 that will produce two free radical drugs 260 from each molecule of ionizable substrate solution 210. In this embodiment, two hydroxyl radicals (free radical drug 260) are produced, in chamber 165, from each molecule of (ionizable substrate solution 210 (hydrogen peroxide). In step 315, the pump control apparatus 235 is activated by switch 265, expelling the free radical drug 260 into the treatment area 280 via applicator 166. In step 315, a free radical drug 260 in the volume range of microliters is dispensed, although any practical volume may be produced. At the same time, activation of the pump apparatus 235 in step 305 also advances the next precise, metered dose of ionizable substrate solution 210 into chamber 165. In step 316, the physician determines whether additional doses of the free radical drug 260 are desired. If the production of additional free radical drug 260 is desired, the physician may repeat steps 313 through 315 to generate additional doses. Otherwise, the method advances to step 317, where the physician may repeat steps 312-316 as desired to achieve the overall treatment plan. Steps 313 to 315 typically treat an area in the range of tens to hundreds of cubic millimeters ($mm^3$) based on metered doses in the range of microliters. Steps 312-317 allow the treatment of any practical-size treatment area 280. The procedure terminates at step 318 and the post-procedure and post-care of the patient begins.

The disclosed systems and methods allow for the production of a precise concentration and volume of a free radical drug solution which may immediately thereafter be injected into the treatment area. In one embodiment, the systems and methods produce a hydroxyl radical drug solution. In an additional embodiment, the treatment dose volume is in the range of several microliters, although any practical quantity can be produced and delivered by systems 150, 160, 190 and 250.

The blood-brain-barrier (BBB) is a natural filter that prevents many undesired substances from reaching the brain. Many chemotherapy drugs are on the order of 200 to 1,200 Daltons and cannot pass to the brain without suppression of the BBB. Suppression of the BBB allows passage of solutes 10 to 100 times larger than normal. However, this process allows undesired solutes, proteins, and pathogens to pass. BBB suppression drugs also may cause dangerous swelling of the brain. One advantage of the methods described herein and the resulting locally in vivo produced hydroxyl radical is the patient's BBB is not a factor, thus simplifying treatment of diseases which affect the brain, such as GBM. The hydroxyl radical is 40% smaller than the smallest nanoparticle, with a diameter of roughly 400 pm, or 17 Daltons.

An additional advantage of the presently disclosed systems and methods is the ability to treat aggressive and advanced cancers after the exhaustion of other treatment options. For example, current GBM tumor therapy treatment cycles typically involve surgery, radiotherapy, and chemotherapy. Survival upon GBM tumor recurrence is typically less than six months as the patient's failing health prevents further treatment options. The presently disclosed systems and methods cause little or no adverse systemic effects while allowing frequent outpatient treatments as often as every few months, greatly extending patient survival time.

An added benefit of the described systems and methods is that unlike current chemotherapeutic treatment methodologies, the localized in vivo development of free radicals, for example hydroxyl radicals, causes very little or no systemic effects. The produced free radicals may be targeted directly at the diseased tissues with minimal impact to surrounding healthy tissues. In addition, the methods of generating and administering the free radicals are relatively simple when compared to conventional chemotherapy or radiotherapy techniques. Therefore, treatment may often be administered at a physician's office or mobile facilities. The infrastructure needed to support the presently described systems and methods is readily available. Surgeons and many physicians already possess the necessary skills to administer the therapy. Outpatient surgical care facilities already have access to the required external imaging equipment. This localized free radical treatment method is compatible with existing chemotherapy and radiotherapy techniques and may be used in conjunction with these methods. Diseased tissue cannot develop a tolerance to free radicals. Simple counter measures are available to prevent the free radicals from affecting surrounding healthy tissues, such as the use of antioxidants vitamins C and E. These methods and systems are very inexpensive as compared to conventional cancer treatment methods and have very low risks compared to these other options. Additional applications of the presently described systems and methods may include non-cancer therapies, for example cosmetic and surgical skin treatments.

Accordingly, the benefits of these disclosed systems and methods allow for localized treatment modalities capable of killing any identifiable diseased tissue. The complexity of these methods is on the order of the complexity of a needle biopsy. In many cases, the patient will have already undergone a needle biopsy to confirm the diagnosis of the disease. In some cases, a needle biopsy may be performed concurrently with the presently described methods.

The free radicals of the present disclosure are optimum chemotherapy drugs. Most free radicals, for instance hydroxyl radicals, are extremely chemically-reactive, making their production and use outside of the human body risky. Currently, delivery of hydroxyl radicals inside diseased tissue is accomplished only through the use of radioactive ionizing radiation. The production of free radicals via radiotherapy is well established and the pharmacology is clearly understood. However, radiotherapy exposes healthy and diseased tissue to the radioactive radiation with short- and long-term systemic consequences. The methods and systems described in the current disclosure provide for the in vivo development and delivery of free radicals directly to the patient's tissue without systemic affects or exposure to radioactive ionizing radiation.

Now, therefore, the following is claimed:

1. A method of producing and administering a therapeutic drug to a patient, said method comprising:
   piercing the skin of the patient and positioning an ionizable substrate drug delivery apparatus at a treatment area inside a tissue of the patient;
   directing an ionizable substrate solution into a chamber of the ionizable substrate drug delivery apparatus;
   exposing the ionizable substrate solution to ionizing radiation in the chamber, thereby converting the ionizable substrate solution to free radicals; and
   injecting the free radicals into said tissue of the patient wherein:
   the ionizable substrate delivery apparatus comprises:
   an outer cannula configured for piercing the skin of the patient;
   a body defining an inner chamber for receiving an ionizable substrate solution;
   a structure within the inner chamber for transmitting ionizing radiation to the ionizable substrate solution in the chamber thereby developing a free radical drug; and
   an applicator for directing the free radical drug from the chamber to a treatment site.

2. The method of claim 1, wherein said injecting the free radicals into said tissue comprises injecting a total volume of at least one microliter and less than one milliliter.

3. The method of claim 1, further comprising generating the ionizing radiation with a light emitting diode.

4. The method of claim 1, further comprising directing the ionizable substrate solution to the chamber with a pressure control element.

5. The method of claim 1, wherein the ionizable substrate solution comprises hydrogen peroxide.

6. The method of claim 1, wherein the exposing comprises exposing the ionizable substrate solution to ultraviolet subtype C radiation.

7. The method of claim 6, wherein the ultraviolet subtype C radiation is at a wavelength of about 220 nm.

8. The method of claim 1, wherein a total volume of said tissue into which the free radicals are injected is less than one cubic centimeter.

9. The method of claim 1, further comprising directing the free radicals through an applicator positioned on an anterior end of the ionizable substrate drug delivery apparatus.

10. The method of claim 1, wherein the exposing occurs while the ionizable substrate drug delivery apparatus is inserted into patient tissue.

* * * * *